(12) United States Patent
Marquais-Bienewald et al.

(10) Patent No.: US 8,221,508 B2
(45) Date of Patent: Jul. 17, 2012

(54) POLYMERIC HAIR DYES

(75) Inventors: Sophie Marquais-Bienewald, Hegenheim (FR); Christian Cremer, Lörrach (DE); Olof Wallquist, Bottmingen (CH); Xian-Zhi Zhou, Leonia, NJ (US); Barbara Wagner, Lörrach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/133,234

(22) PCT Filed: Dec. 4, 2009

(86) PCT No.: PCT/EP2009/066421
§ 371 (c)(1),
(2), (4) Date: Jul. 19, 2011

(87) PCT Pub. No.: WO2010/079025
PCT Pub. Date: Jul. 15, 2010

(65) Prior Publication Data
US 2011/0296631 A1 Dec. 8, 2011

(30) Foreign Application Priority Data
Dec. 15, 2008 (EP) ..................................... 08171619

(51) Int. Cl.
*A61Q 5/10* (2006.01)
*C07D 213/22* (2006.01)
(52) U.S. Cl. ............. 8/405; 8/552; 8/554; 8/647; 8/657; 546/264
(58) Field of Classification Search ............. 8/405, 552, 8/554, 647, 657; 546/264
See application file for complete search history.

(56) References Cited

U.S. PATENT DOCUMENTS

| 4,182,612 A | 1/1980 | Sokol |
| 4,228,259 A | 10/1980 | Kalopissis |
| 6,306,182 B1 | 10/2001 | Chan |

FOREIGN PATENT DOCUMENTS

| FR | 2456764 A2 | 12/1980 |
| WO | 2008009579 A | 1/2008 |
| WO | WO 2008/009579 A1 * | 1/2008 |

OTHER PUBLICATIONS

English language abstract of FR 2456764 AN:1981:499329.

\* cited by examiner

*Primary Examiner* — Eisa Elhilo
(74) *Attorney, Agent, or Firm* — Shiela A. Loggins

(57) ABSTRACT

Polymeric dye comprising oligo and polypeptides selected from natural or synthetic aminoacids bearing at least one covalently bounded cationic dye. Very good dyeing results on human hair are obtained with these dyes.

20 Claims, No Drawings

POLYMERIC HAIR DYES

The present invention relates to novel polymeric dyes and compositions comprising these compounds, to a process for their preparation and to their use for dyeing of organic materials, such as keratin-containing fibers, wool, leather, silk, cellulose or polyamides.

It is well known that cationic compounds have a good affinity to negative charged hair. These characteristics have been used to contact the hair with small molecules, but also with polymers.

Numerous cationic polymeric dyes have been disclosed for use as a colorant for human hair, for example in U.S. Pat. No. 4,228,259, U.S. Pat. No. 4,182,612 or FR 2 456 764. These references teach that the polymer moiety has the cationic charge.

Surprisingly it was found that very good dyeing results are obtained with polymeric hair dyes wherein the cationic charge is located in the dye moiety.

More specifically it was found surprisingly that very good dyeing results and washing fastness are obtained with oligo and polypeptides hair dyes wherein the cationic charge is located on the dye moiety.

Therefore the present invention relates to polymeric dyes comprising oligo and polypeptides selected from natural or synthetic aminoacids comprising at least one covalently bounded cationic dye.

Preferably these polymeric dyes correspond to the formulas

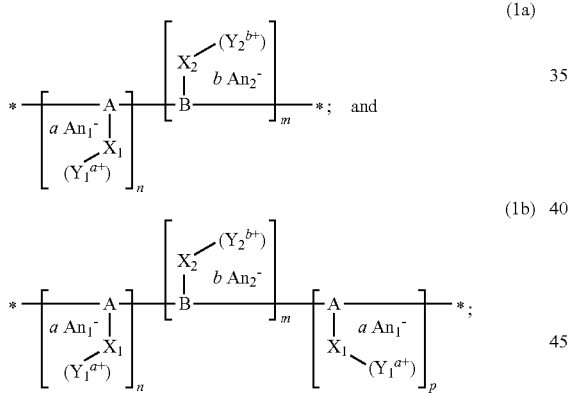

wherein
A and B, independently from each other represent a polymer backbone selected from a natural or synthetic amino carboxylic acid;
$X_1$ and $X_2$ independently from each other are a linkage group selected from —$C_1$-$C_{30}$alkylene-, —$C_2$-$C_{12}$alkenylene-, or —$C_6$-$C_{10}$arylene- which is interrupted and/or terminated at one or both ends by one or more than one —O—, —S—, —N—, —N=, —N($R_5$)—, —S(O)—, —SO$_2$—, —(CH$_2$CH$_2$—O)$_{1-5}$—, —(CH$_2$CH$_2$CH$_2$—O)$_{1-5}$—, —C(O)—, —C(O)O—, —OCO—,

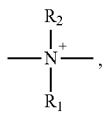

—CON($R_1$)—, —C(N$R_1R_2$)$_2$—, —($R_1$)NC(O)—, —C(S)$R_1$— or

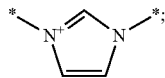

or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen; the direct bond; or a bivalent radical of formula $$-(T)_t(Z)-, \text{wherein} \tag{1c}$$

T is —$C_1$-$C_{12}$alkylene; —$C_2$-$C_{12}$alkenylene-; —C(O)—; —(CH$_2$CH$_2$—O)$_{1-5}$—; —(CH$_2$CH$_2$CH$_2$—O)$_{1-5}$—; —C(O)O—; —OC(O)—; —N($R_3$)—; —CON($R_3$)—; —($R_3$)NC(O)—; —O—; —S—; —S(O)—; —S(O)$_2$—; —S(O)$_2$N($R_3$)—; or —N$^+$($R_3$)($R_4$)—;
Z is a biradical of formula

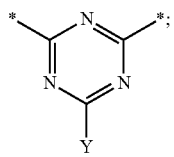

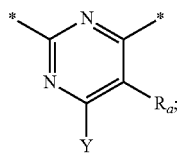

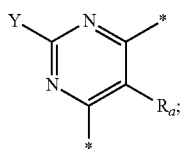

$R_1$, $R_2$, $R_3$, $R_4$ and $R_5$ independently from each other are hydrogen; unsubstituted or substituted, straight-chain or branched, monocyclic or polycyclic, interrupted or uninterrupted $C_1$-$C_{14}$alkyl; $C_1$-$C_{14}$alkoxy; $C_2$-$C_{14}$alkenyl; $C_1$-$C_6$alkylamino; $C_6$-$C_{10}$aryl; $C_6$-$C_{10}$aryl-$C_1$-$C_{10}$alkyl; $C_6$-$C_{10}$aryl-$C_1$-$C_{10}$alkoxy; or $C_5$-$C_{10}$alkyl($C_5$-$C_{10}$aryl);
$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-aryl-amino; SO$_2$$R_3$; chlorine; or fluorine;
Y is $R_a$; $Y_1^{a+}$; or $Y_2^{b+}$;
a and b independently from each other are 1, 2 or 3;
t is 0 or 1;
$Y_1$ and $Y_2$ independently from each other are a residue of an organic dye; or hydrogen; wherein at least one of $Y_1$ and $Y_2$ is a residue of an organic dye;
An$_1$ and An$_2$, independently from each other are an anion;
a and b independently from each other are a number from 1 to 3;

m is a number from 0 to 5000;
n is a number from 0 to 5000; and
p is a number from 1 to 5000;
wherein the sum of m+n+p≧3.

Preferred are dyes of formulae (1a) or (1b), wherein

A and B, independently from each other represent a polymer backbone selected from a natural or synthetic amino carboxylic acid;

$X_1$ and $X_2$ independently from each other are a linkage group selected from —$C_1$-$C_{30}$alkylene- and —$C_2$-$C_{12}$alkenylene-, which is interrupted and/or terminated at one or both ends by one or more than one —S—, —N—, —N═—, —N($R_5$)—, —S(O)—, —$SO_2$—, —($CH_2CH_2$—O)$_{1-5}$—, —($CH_2CH_2CH_2$—O)$_{1-5}$—, —C(O)—, —C(O)O—, —OCO—,

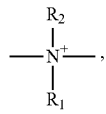

—CON($R_1$)—, —C($NR_1R_2$)$_2$—, —($R_1$)NC(O)—, —C(S)$R_1$—; or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen; the direct bond; or a bivalent radical of formula -(T)$_t$(Z)—, wherein (1c)

T is —$C_1$-$C_{12}$alkylene; —$C_2$-$C_{12}$alkenylene-; —C(O)—; —($CH_2CH_2$—O)$_{1-5}$—; —($CH_2CH_2CH_2$—O)$_{1-5}$—; —C(O)O—; —OC(O)—; —N($R_3$)—; —CON($R_3$)—; —($R_3$)NC(O)—; —O—; —S—; —S(O)—; —S(O)$_2$—; —S(O)$_2$N($R_3$)—; or —$N^+(R_3)(R_4)$—;

Z is a biradical of formula

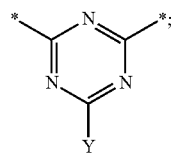 (1d)

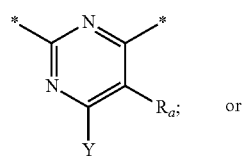 (1e)

or

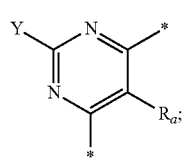 (1f)

$R_1$, $R_2$, $R_3$, $R_4$ and $R_5$ independently from each other are hydrogen; unsubstituted or substituted, straight-chain or branched, monocyclic or polycyclic, interrupted or uninterrupted $C_1$-$C_{14}$alkyl; $C_1$-$C_{14}$alkoxy; $C_2$-$C_{14}$alkenyl; $C_1$-$C_6$alkylamino; $C_6$-$C_{10}$aryl; $C_6$-$C_{10}$aryl-$C_1$-$C_{10}$alkyl; $C_6$-$C_{10}$aryl-$C_1$-$C_{10}$alkoxy; or $C_5$-$C_{10}$alkyl($C_5$-$C_{10}$aryl);

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-aryl-amino; $SO_2R_3$; chlorine; or fluorine;

Y is $R_a$; $Y_1^{a+}$; or $Y_2^{b+}$;

a and b independently from each other are 1, 2 or 3;

t is 0 or 1;

$Y_1$ and $Y_2$ independently from each other are a residue of an organic dye; or hydrogen; wherein at least one of $Y_1$ and $Y_2$ is a residue of an organic dye;

$An_1$ and $An_2$, independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecy, dodecyl, tredecyl or tetradecyl.

$C_2$-$C_{14}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_6$-$C_{10}$aryl is for example phenyl or naphthyl.

$C_1$-$C_{30}$alkylene is for example methylene, ethylene, propylene, isopropylene, n-tetramethylene, sec-tetramethylene, tert-tetramethylene, n-pentamethylene, 2-pentamethylene 3-pentamethylene, 2,2'-dimethylpropylene, cyclopentamethylene, cyclohexamethylene, n-hexamethylene, n-octamethylene, 1,1',3,3'-tetramethyltetramethylene, 2-ethylhexamethylene, nonamethylene, decamethylene, tridecamethylene, tetradecamethylene, pentadecamethylene, hexadecamethylene, heptadecamethylene, octadecamethylene, nonadecamethylene or eicosamethylene.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

In formulae (1a) and (1b) preferably $Y_1$ and $Y_2$ independently from each other are selected from the group of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine, oxazine, perinone, perylene, pyrenequinone, phtalocyanine, phenazine, quinoneimine, quinacridone, quino-phtalone, styryl, stilbene, xanthene, thiazine and thioxanthene dyes.

More preferably, $Y_1$ and $Y_2$ independently from each other are selected from azo, azomethine, hydrazomethine, anthraquinone, merocyanine, methine, oxazine and styryl dyes.

Most preferably $Y_1$ and $Y_2$ have the same meaning.

Preferably in formulae (1a) and (1b) both the polymer backbone (A and B) and residue of an organic dye ($Y_1$ and $Y_2$) have a functional group selected from the electrophilic group selected from halide, tosylate, mesylate, methoxy, carboxylic acid, carboxylic acid chloride, sulfonyl chloride, epoxides, anhydride; or a nucleophilic group selected from amine, guanidine, hydroxyl and thiol.

Even more preferred are dyes of formulae (1a) and (1b), wherein the polymer backbone (A and B) is selected from histidine, arginine, cysteine, glutamine, glutaminic acid, lysine, asparagine, serine, tyrosine, threonine, tryptophane and proline.

Most preferred polymer backbones are polylysine, polyaspartic acid, polyglutamic acid and polyasparagin.

Preferably the molecular weight of the polymeric dye is from 400 to 50000.

Most preferably are polylysines modified with a $X_1$-$(Y_1^{a+})$ dye moiety in α and/or ε position, which correspond for example to the formula

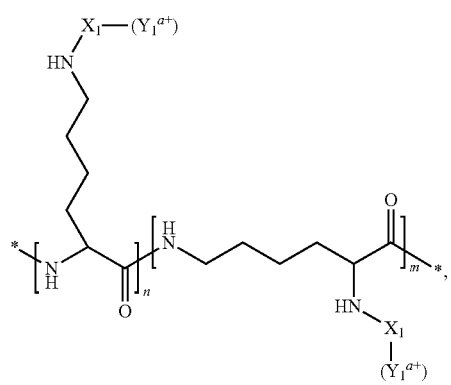

(2)

wherein $X_1$, $Y_1$, m, n and a are defined as in formulas (1a) and (1b).

It is also possible that some amino functionalities of the polymeric backbone can also stay unreacted.

The polymeric dye of formula (2) is obtained by

1. Synthesis of a polylysine from lysine and

2. Reaction of that polylysine with a dye of formula $(Y_1^{a+})$—$X_1$—Z, $Y_1$, Z is a reactive leaving group such as a halide, methoxy, tosylate:

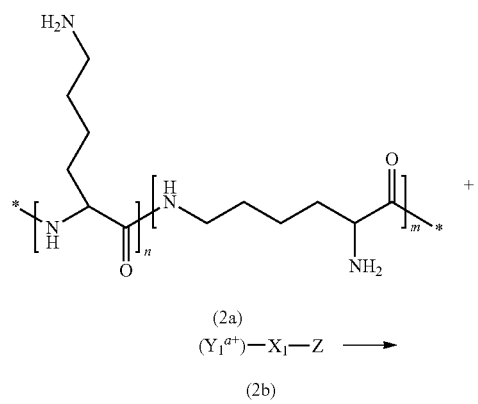

(2a)

$(Y_1^{a+})$—$X_1$—Z ⟶

(2b)

-continued

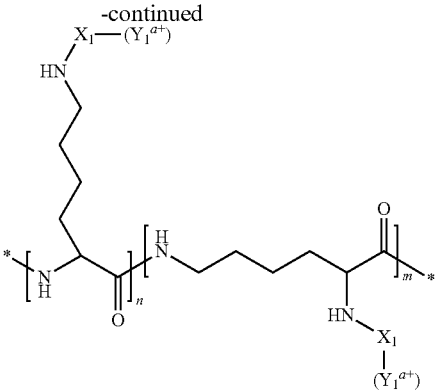

(2)

The reaction may be carried out in solvents like water, alcohols, like methanol, ethanol, 2-propanol or butanol; nitriles, like acetonitrile or propionitrile; amides, like dimethylformamides, dimethylacetamide, N-methylpyrolidone; chlorinated hydrocarbons like chloroform, chlorobenzene or trichloroethylene; or other solvents like dimethylsulfoxide.

Customary, the temperature is in the range of 0 to 200° C., preferably 20 to 110° C. during the mixing of the starting compounds.

The reaction time is generally dependent on the reactivity of the starting compounds, on the selected reaction temperature and on the desired conversion. The selected reaction time is usually in the range from three hours to seven days.

The selected reaction pressure is generally in the range from 0.1 to 10 bar especially from 0.2 to 3.0 bar and is more especially atmospheric pressure.

It may be desirable to conduct the reaction of compounds in the presence of a catalyst. Suitable catalysts are for example an alkali or transition metal $C_1$-$C_6$alkyloxide, such as sodium-, potassium or lithium $C_1$-$C_6$alkyloxide, preferably sodium methoxide, potassium m-thoxide or lithium methoxide, or sodium ethoxide, potassium ethoxide or lithium ethoxide; or secondary or tertiary amine, such as chinuclidine, piperidine, N-methylpiperidine, pyridine, trimethylamine, dimethylamine, diethylamine, triethylamine, trioctylamine, 1,4-diazabicyclo-[2.2.2]octan, chinuclidine, N-methylpiperidine; or alkalimetal acetate, for example such as sodium acetate, potassium acetate, or lithium acetate.

The molar ratio of the dye of formula (2a) to polylysine monomer is generally selected in the range from 0.1:1 to 3:1, especially in the range from 0.1:1 to 1.5:1.

The product prepared according to the process of the present invention may be advantageously worked up and isolated, and if desired be purified.

Customary, the work up starts by decreasing the temperature of the reaction mixture in the range from 5 to 80° C., especially in the range from 20 to 50° C.

It may be advantageous to decrease the temperature slowly, over a period of several hours.

In general, the reaction product is usually filtered off and then washed with water, with a solvent or with a salt solution and subsequently dried.

Filtration is normally carried out in standard filtering equipment, for example Bühner funnels, filter presses, pressurised suction filters, preferably in vacuo.

The temperature for the drying is dependent on the applied pressure. Drying is usually carried out in vacuo at 50-200 mbar. The drying is usually carried out at a temperature in the range from 40 to 90° C.

Advantageously the product is purified by recrystallisation after isolation. Organic solvents and solvent mixtures are suitable for the recrystallisation.

The dyes of formula (1a) and (1b) according to the present invention are suitable for dyeing organic materials, such as keratin-containing fibers, wool, leather, silk, cellulose or polyamides, cotton or nylon, and preferably human hair including body hairs like eyebrows, eyelashes, pubic-, breast-, armpit- and beard hair. Also animal hair can be colored with the inventive hair dyes.

The dyeings obtained are distinguished by their depth of shade and their good fastness properties to washing, such as, for example, fastness to light, shampooing and rubbing.

Generally, hair dyeing agents on a synthetic base may be classified into three groups:
- temporary dyeing agents
- semipermanent dyeing agents, and
- permanent dyeing agents.

The multiplicity of shades of the dyes can be increased by combination with other dyes.

Therefore the dyes of formula (1a) and (1b) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1a) and (1b) may be used in combination with at least one single direct dye different from the dyes of formula (1a) and (1b).

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie- und Handelsunternehmen für Arzneimittel, Reformwaren und Körperpflegemittel e. V., Mannheim.

More preferred direct dyes which are useful for the combination with at least one single dye of formula (1a) and (1b), especially for semi permanent dyeing, are:
2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3yl)-azo)pyridine, 2-nitro-5-glyceryl-methylanil, 3-methylamino-4-nitro-phenoxyethanol, 4-amino-2-nitrodiphenyleneamine-2'-carboxilic acid, 6-nitro-1,2,3,4-tetrahydroquinoxal, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethyl-aminophenol, 4-amino-3-nitrophenol, 4-hydroxypropylamine-3-nitrophenol, hydroxyanthryl-aminopropylmethyl morphlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylenediamine, HC Violet BS, Picramic Acid, Solvent Green 7.

The inventive polymeric hair dyes do not require any addition of an oxidizing agent to develop their dyeing effect. This fact could possibly reduce the damage of the hair. In addition many of the perceived or documented disadvantages of current oxidative hair dyes like their skin irritation, skin sensibilization and allergenic properties can be prevented by the use of the inventive hair dyes. Also, the inventive hair dyes are easier to apply and to use in formulations than oxidative hair dyes since no chemical reaction occurs upon application on the head. Especially advantageous is the fact, that the dyeing time is significantly shorter (ca. 5-10 min) than dyeing using oxidative dyes.

Furthermore, the dyes of formula (1a) and (1b) may be combined with at least one cationic azo dye, for example the compounds disclosed in GB-A-2 319 776 as well as the oxazine dyes described in DE-A-299 12 327 and mixtures thereof with the other direct dyes mentioned therein.

The dyes of formula (1a) and (1b) may also be combined with acid dyes, for example the dyes which are known from the international names (Color index), or trade names.

The dyes of formula (1a) and (1b) may also be combined with uncharged dyes.

Furthermore, the dyes of formula formula (1a) and (1b) may also be used in combination with oxidation dye systems.

Oxidation dyes, which, in the initial state, are not dyes but dye precursors are classified according to their chemical properties into developer and coupler compounds.

Suitable oxidation dyes are described for example in
DE 19 959 479, especially in col 2, l. 6 to col 3, l. 11;
"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraaminopyrimidine derivatives, or unsaturated aldehydes as described in DE 19 717 224, especially on p. 2, l. 50 to l. 66 and on p. 3 l. 8 to l. 12, or cationic developer compounds as described in WO 00/43367, especially on p., 2 l. 27 to p. 8, l. 24, in particular on p. 9, l. 22 to p. 11, l. 6.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

More preferred developer compounds are p-phenylendiamine, p-toluylendiamine, p-, m- o-aminophenol, N,N-bis-(2-hydroxyethyl)-p-phenylenediamine sulfate, 2-amino-4-hydroxy-ethylaminoanisole sulfate, hydroxyethyl-3,4-methylenedioxyanil, 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraaminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

Furthermore, autooxidizable compounds may be used in combination with the dyes of formula formula (1a) and (1b).

The dyes of formula formula (1a) and (1b) may also be used in combination with naturally occurring dyes.

Furthermore, the dyes of formula formula (1a) and (1b) may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference on p. 3 to 5.

Furthermore, the dyes of the present invention can also be combined with dyes which are prepared by the reaction of a reactive carbonyl-compound and a CH-acidic compound as described in DE 10 2006 062 435 A1, WO 00038638, DE 10241076 and WO 05120445;
  with thiadiazol dyes as described in DE 10 2006 036898 and DE 10 2005 055496,
  with fluorescent stilbenic sulphur dyes as described in for example WO 07110532, WO 07110542,
  with tetraazapentamethine dyes as described in WO 07071684 and WO 07071686,
  with dimeric cationic dyes as described in FR 2879195, FR 2879127, FR 2879190, FR 2879196, FR 2879197, FR 2879198, FR 2879199, FR 2879200, FR 2879928, FR 2879929, WO 06063869,
  with azo and styryl dyes as described in EP 0850636,
  with polymeric anionic dyes as described in FR 2882929,
  with disulfide dyes as described in WO 0597051, EP 1647580, WO 06136617,
  with thiol dyes as described in WO 07025889, WO 07039527, and
  with conductive polymers as described in US 20050050650, U.S. Pat. No. 7,217,295

The present invention also relates to formulations, which are used for the dyeing of organic materials, preferably keratin-containing fibers, and most preferably human hair, comprising at least one dye of formula (1a) and (1b).

Preferably the dyes of formula formula (1a) and (1b) are incorporated into the composition for treating organic material, preferably for dyeing in amounts of 0.001-5% by weight (hereinafter indicated merely by "%"), particularly 0.005-4%, more particularly 0.1-3%, based on the total weight of the composition.

The dyeing compositions of the present invention are applied on the hair in a temperature range of 10 to 200, preferably 18 to 80, and most preferably from 20 to 40° C.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations of from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, l. 1 to p. 244, l. 12.

If the dyes of formula (1a) and (1b) are used together with oxidation dyes and/or the addition salts thereof with an acid, they may be stored separately or together. Preferably the oxidation dyes and the direct dyes which are not stable to reduction or base are stored separately.

The dyes of formula (1a) and (1b) may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuavents are preferably used in the hair dyeing compositions of the present invention: -non-ionic polymers, cationic polymers, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers; -quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilisers, anti-dandruff active ingredients, substances for adjusting the pH value, panthenol, pantothenic acid, allantoin, pyrrolidone carboxylic acids and salts thereof, plant extracts and vitamins, cholesterol; -light stabilisers and UV absorbers, consistency regulators, fats and waxes, fatty alkanolamides, polyethylene glycols and polypropylene glycols having a molecular weight of from 150 to 50,000, complexing agents, swelling and penetration substances, opacifiers, pearlising agents, propellants, antioxidants, sugar-containing polymers, quaternary ammonium salts and bacteria inhibiting agents.

The dyeing compositions according to the present invention generally comprise at least one surfactant. Suitable surfactants are zwitterionic or ampholytic, or more preferably anionic, non-ionic and/or cationic surfactants.

A further embodiment of the present invention relates to the dyeing of keratin-containing fibers.

The processes comprises
(a) treating the keratin-containing fiber with at least one dye of formula (1a) and (1b) and
(b) leaving the fiber to stand and then rinsing the fiber.

The dyes of formula (1a) and (1b) are suitable for all-over dyeing of the hair, that is to say when dyeing the hair on a first occasion, and also for re-dyeing subsequently, or dyeing of locks or parts of the hair.

The dyes of formula (1a) and (1b) are applied on the hair for example by massage with the hand, a comb, a brush, or a bottle which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1a) and (1b), a base and an oxidizing agent.

A preferred embodiment for dyeing keratin-containing fibers, in particular human hair, with a dye of formula (1a) and (1b) and an oxidizing agent, comprises
$a_1$) treating the keratin-containing fiber with the oxidizing agent, which optionally contains at least one dye of formula (1a) and (1b),
$b_1$) treating the keratin-containing fiber with an oxidizing agent free composition, which optionally contains at least one dye of formula (1a) and (1b); or alternatively
$a_2$) treating the keratin-containing fiber with an oxidizing agent free composition, which optionally contains at least one dye of formula (1a) and (1b);
$b_2$) treating the keratin-containing fiber with an oxidizing agent, which optionally contains least one dye of formula (1a) and (1b),
with the proviso that at least in one of the process steps $a_1$), $a_2$), $b_1$) or $b_2$) a dye of formula (1a) and (1b) is present.

In general, the oxidizing agent containing composition is left on the fiber for 0 to 45 minutes, in particular for 15 to 30 minutes at 15 to 45° C.

The oxidizing agent free composition usually comprises customary adjuvants and additives. Preferred are those, which are described in German Patent Application, in col 3, I. 17 to I. 41.

In general, the dye of formula (1a) and (1b) and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of formula (1a) and (1b) which are stable to reduction can be stored together with the oxidizing agent free compositions and may be applied as a single composition.

Advantageously the compositions comprising a dye of formula (1a) and (1b) which are not stable to reduction are prepared with the oxidizing agent free composition just before the dyeing process.

In a further embodiment, the dye of formula (1a) and (1b) and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are
oxidizing agents to achieve lightened coloration, as described in WO 97/20545, especially p. 9, I. 5 to 9,
oxidizing agents in the form of permanent-wave fixing solution, as described in DE-A-19 713 698, especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 3%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

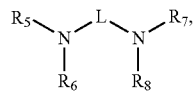

wherein
L is a propylene residue, which may be substituted with OH or $C_1$-$C_4$alkyl; and
$R_5$, $R_6$, $R_7$ and $R_8$ independently or dependently from each other are hydrogen; $C_1$-$C_4$alkyl; or hydroxy-$(C_1$-$C_4)$alkyl.

The pH-value of the oxidizing agent containing composition is usually about 2 to 7, and in particular about 2 to 5.

One preferred method of applying formulations-comprising the dyes of formula (1a) and (1b) on the keratin-containing fiber, preferably the hair is by using a multi-compartment dyeing device or "kit" or any other multi-compartment packaging system, as described for example in WO 97/20545 on p. 4, l. 19 to l. 27.

Generally the hair is rinsed after treatment with the dyeing solution and/or permanent-wave solution.

A further preferred embodiment of the present invention relates to a method of dyeing hair with oxidative dyes, which comprises a. mixing at least one dye of formula (1a) and (1b) and optionally at least one coupler compound and at least one developer compound, and an oxidizing agent, which optionally contains at least one further dye, and
b. contacting the keratin-containing fibers with the mixture as prepared in step a.

For adjusting the pH-value organic or inorganic acids, as for example described in DE 199 59 479, col 3, l. 46 to l. 53 are suitable.

Furthermore, the present invention relates to a process of dyeing of keratin-containing fibers of the dyes of formula (1a) and (1b) with autooxidable compounds and optionally further dyes.

The process comprises a. mixing at least one autooxidable compound and at least one developer compound and at least one dye of formula (1a) and (1b) and optionally further dyes, and
b. treating the keratin-containing fiber with the mixture prepared in step a.

Furthermore, the present invention relates to a process for dyeing keratin-containing fibers with the dyes of formula (1a) and (1b) and capped diazotised compounds, which comprises, a. treating the keratin-containing fibers under alkaline conditions with at least one capped diazotised compound and a coupler compound, and optionally a developer compound ad optionally an oxidizing agent, and optionally in the presence of a further dye, and optionally with at least one dye of formula (1a) and (1b), and
b. adjusting the pH in the range of 6 to 2 by treatment with an acid, optionally in the presence of a further dye, and optionally at least one dye of formula (1a) and (1b), with the proviso that at least in one step a. or b. at least one dye of formula (1a) and (1b) is present.

The capped diazotised compound and coupler compound and optionally the oxidizing agent and developer compound can be applied in any desired order successively or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the dyes of formula (1a) and (1b) and at least one acid dye.

The following examples serve to illustrate the processes for dyeing without limiting the processes thereto. Unless specified otherwise, parts and percentages relate to weight. The amounts of dye specified are relative to the material being dyed.

PREPARATION EXAMPLES

Example A1

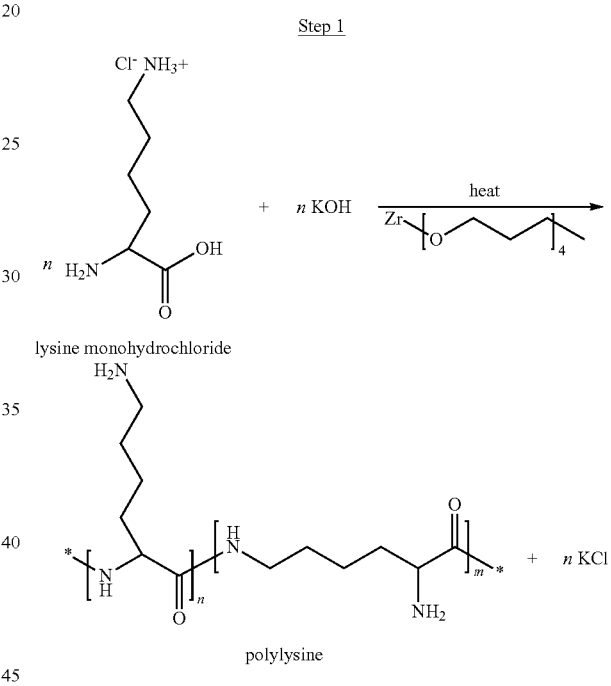

Preparation Method:

A mixture of L-lysine HCl (50 g, 274 mmol) and KOH (15.36 g, 274 mmol) are introduced into an open 3 necked round bottom flask equipped with a mechanic stirrer. 5 mL water is added and the mixture is stirred until it has a pulplike consistence and subsequently heated to 150° C. When the mixture id melted, Zr(O"Bu)$_4$ (4 mL, 80 wt %, 3 mol % with respect to the L-lysine monomer) is added as catalyst and hold for 0.5 h.

The mixture is then heated up to 180° C. for 3 h.

The water that formed during the polymerization is allowed to escape from the open reactor.

The resultant brown solid is dissolved in water.

The insoluble impurities are removed by filtration and the aqueous solution is lyophilized to afford the polymer (A1) as a yellow-brown solid.

Mw 2.68 k; Mn 1.4 k

1H NMR (MeOD-d6): δ[ppm] 4.3 (br, 1H), 4.0 (br, 2H), 3.4-3 (br, 17H including MeOD), 2.8 (m, 9H), 2-1.1 (br, 111H)

Example A2

(P 1)

The synthesis of the intermediate P1 is described in IP.com Journal (2004), 4(9), 31.

2.2 g of the polylysine.KCl obtained in Example A1 are reacted with 0.255 g of the fluoride derivative P1 (1 mmol) in 5 ml methanol at room temperature for 2 days. After reaction, the precipitated salts are eliminated by filtration and the methanolic solution is evaporated under vacuum (1 mbar) to afford 2.7 g of the red polymer (A2).

Example A3

2.2 g of the polylysine.KCl obtained in Example A1 are reacted with 0.637 g of the fluoride derivative P1 (2.5 mmol) in 5 ml methanol at room temperature for 7 days.

After reaction, the precipitated salts are eliminated by filtration and the methanolic solution is evaporated under vacuum (1 mbar) to afford 2.587 g of the red polymer (A3).

1H NMR (MeOD-d6): δ[ppm] 8-7.8 (br, 1H), 7.6-7.45 (br, 1H), 6.95-6.75 (br, 1H), 4.6-3.85 (br, 3.5H), 3.7-2.75 (br 17H including solvent), 2.2-0.9 (br, 13H)

Example A4

(P 2)

The synthesis of the intermediate P2 is described in WO 2004/7083312.

1.1 g of the polylysine.KCl obtained in Example A1 are reacted with 0.133 g of the methoxy derivative P2 (0.5 mmol) in 5 ml methanol at room temperature for 2 days.

After reaction, the precipitated salts are eliminated by filtration and the methanolic solution is evapored under vacuum (1 mbar) to afford 712 mg of the red polymer (A4).

Examples A5 and A6

(A5)

Example A5

A mixture 1.27 g of 1,4-Bis[(3-chloro-2-hydroxypropyl)amino]-9,10-anthracenedione (30 mmol) prepared as described in *J. Med. Chem* 1992, vol. 35, n° 23, 4259-4263 in 12.7 ml of pyridine and 12.7 ml of toluene are heated at 100° C. under nitrogen atmosphere for 2 days. After cooling the reaction mixture was evaporated to dryness and recrystallized with a mixture of dioxane and methanol (1/1). The solid was filtered and washed with dioxan. After drying, 1.08 g of a dark blue powder (A5) is obtained yielding 72%.

MS (ES+): m/z 465. 1H NMR (dmso-d6): δ[ppm] 10.95 (s, 1H), 9.03 (d, 2H), 8.60 (t, 1H), 8.25 (m, 2H), 8.20 (t, 2H), 7.8 (m, 2H), 7.6 (dd, 2H), 6.05-5.75, (br, 2H), 4.9 (d, 1H), 4.5 (m, 1H), 4.2 (br 1H), 3.9 (br, 1H), 3.8-3.4 (br, 6H)

Example A6

441 mg of the poylysine.KCl A1 (2 meq. NH$_2$) and 251 mg of (A5) (1 mmol) are solubilized in 3 ml DMSO.

The reaction mixture is stirred for 16 h at room temperature and 3 days at 100° C. After cooling, the reaction mixture is precipitated in 40 ml ethyl acetate. The solid is filtered off and washed twice with ethyl acetate. After drying under vacuum 615 mg of a dark blue powder (A6) is obtained.

1H NMR (MeOD-d6): δ[ppm] 9.05 (br, 2H), 8.65 (br, 1H), 8.32 (br, 1H), 8.15 (br, 3H), 7.8 (br, 2H), 7.75-7.5 (br, 2) 4.8-2.9 (br, including MeOD), 2-1.3 (br 17H)

Examples A7

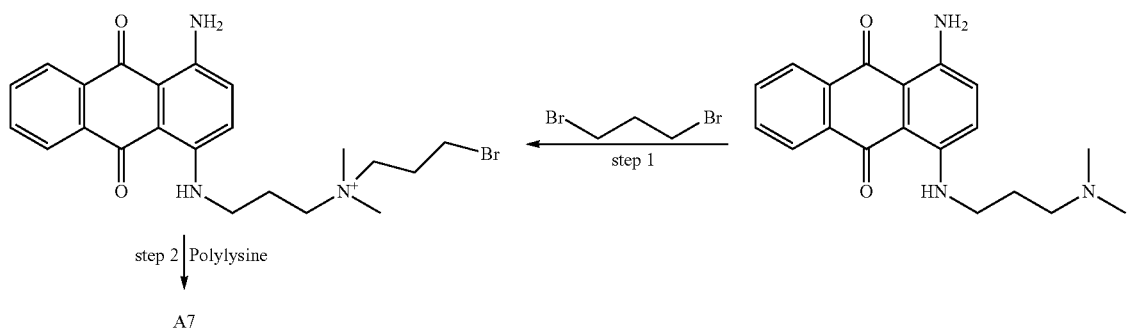

Example A8

Step 1

A solution of 2.37 g 1-amino-4-(3-dimethylaminopropyl) amino-anthraquinone (prepared as described in DE 2927520) and 7.5 ml dibromopropane in 30 ml of chloroform are stirred for 16 h at 60° C. After cooling of the reaction mixture to room temperature, the product is filtered off and dried under vacuum at 30° C. to yield 3.25 g of a blue powder (A7).

MS (ES+): m/z 444, 446. UV/VIS (methanol): λmax 603 nm. 1H NMR (dmso-d6): δ[ppm] 10.84 (t, H), 8.45 (br, 2H) 8.24 (m, 2H) 7.82 (m, 2H), 7.50 (d, 2H), 7.37 (d, 2H), 3.59 (m, 2H), 3.52 (m, 2H), 3.43 (m, 4H), 3.10 (s, 6H), 2.30 (m, 2H), 2.10 (m, 2H).

Step 2

552 mg of the poylysine.KCl A1 (2.5 meq. NH2) and 525 mg of the compound prepared in step 1 (A7) (1 mmol) are solubilized in a mixture of 2 ml methanol and 3 ml of acetonitrile at 70° C. The reaction mixture is stirred for 3 days at 70° C. After cooling, the reaction mixture was precipitated in 30 ml ethyl acetate. The solid was filtered and washed twice with ethyl acetate. After drying under vacuum 306 mg of a dark blue powder (A8) are obtained.

1H NMR (dmso-d6): δ[ppm] 10.9 (br, 1H), 8.5-7.8 (br, 4H), 7.65 (br, 2H), 7.35 (br, 1H), 7.2 (br, 1H), 3.8-2.7 (br, 43H), 2.7-2.5 (br, 2H), 2.1-1 (br, 20H)

Example A9

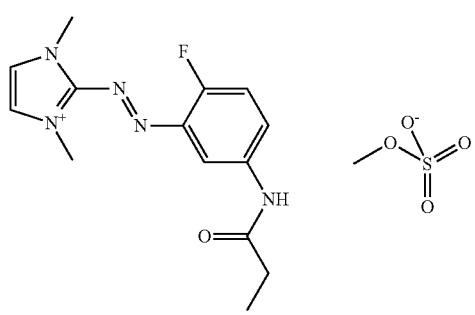

(P 3)

The synthesis of the fluoro building block (P3) is described in the patent WO2006136617.

552 mg of the poylysine.KCl A1 (2.5 meq. NH2) and 521 mg of B (1 mmol) are solubilized in 5 ml methanol and stirred for 5 days at room temperature. The reaction mixture is precipitated in 40 ml ethyl acetate, the solid was filtered and washed twice with ethyl acetate. After drying under vacuum 578 mg of a dark blue powder (A9) are obtained.

1H NMR (MeOD-d6): δ[ppm] 8.56.8 br, 4.4-3.5 br; 3.-0.9 br

B. Application Example

Hair Samples

For the application examples the following hair types have been used:

1 blonde hair tress (VIRGIN White Hair fro IMHAIR Ltd., via G. Verga 8, 90134 Palermo (Italy)), 1 middle blonde hair tress (UNA-Europ. nature hair, Color middle blonde from Fischbach & Miller, Postfach 1163, 88461 Laupheim, Germany), 1 bleached hair tress (UNA-Europ. nature hair, Color white bleached blonde from Fischbach & Miller, Postfach 1163, 88461 Laupheim, Germany).

Coloring Solution:

0.2 or 1% w/w of one of the dyes described in examples A1 to A5 are dissolved in a Plantaren solution (10% w/w Plantacare 200UP (ID: 185971.5) in water; pH adjusted to 9.5 with 50% citric acid solution or monoethanolamine solution).

The hair tresses are dyed according to the following procedure:

The coloring solution is applied directly to the dry hair, incubated for 20 min. at room temperature, and then rinsed off under tap water (water temperature: 37° C.+/−1° C.; flow rate of water: 5-6 l/min.). Then it is pressed out with a paper towel and dried over night at room temperature on a glass plate.

For the determination of the wash fastness two sets of hair tresses are dyed under the same conditions. One set of the dyed tresses is washed with a commercial shampoo (GOLD-WELL definition Color & Highlights, color-conditioner shampoo) using approx. 0.5 g shampoo for each tress under tap water (water temperature: 37° C.+/−1° C.; flow rate 5-6 l/min).

Finally the tresses are rinsed under tap water, pressed out with a paper towel, combed and dried with a hair dryer or at room temperature. This procedure is repeated 10 times.

Then the color loss of the set of washed tresses relative to the set of unwashed tresses is evaluated using the Grey Scale (from 1 to 5 with 5 being completely unchanged) according to: Industrial Organic Pigments by Herbst&Hunger, $2^{nd}$ ed., p. 61, Nr 10: DIN 54 001-8-1982, "Herstellung and Bewertung der Änderung der Farbe", ISO 105-A02-1993.

TABLE 1

Coloration results

| Example | Dye | wt % dye in plantaren | Hair Type | Color | Intensity | Brilliance | Washfastness |
|---|---|---|---|---|---|---|---|
| B1 | A2 | 0.1 | blond | red | moderate | good | 4-5 |
| | | | middle blond | red | moderate | good | 4-5 |
| | | | bleached | red | moderate | good | 4-5 |
| B2 | A2 | 0.3 | blond | red | good | good | 4-5 |
| | | | middle blond | red | good | good | 4-5 |
| | | | Bleached | red | good | good | 4 |
| B3 | A3 | 0.1 | blond | red | good | good | 4-5 |
| | | | middle blond | red | good | good | 4-5 |
| | | | Bleached | red | good | good | 4-5 |
| B4 | A3 | 0.3 | blond | red | good | good | 4-5 |
| | | | middle blond | red | good | good | 4 |
| | | | Bleached | red | good | good | 4-5 |
| B5 | A4 | 0.1 | blond | red | good | good | 4-5 |
| | | | middle blond | red | good | good | 4 |
| | | | Bleached | red | good | good | 4-5 |
| B6 | A6 | 0.1 | blond | blue | good | good | 4 |
| | | | middle blond | blue | good | good | 4 |
| | | | Bleached | blue | good | good | 3-4 |
| B7 | A7 | 0.1 | blond | blue | good | good | 4 |
| | | | middle blond | blue | good | good | 3-4 |
| | | | Bleached | blue | good | good | 3 |
| B8 | A8 | 0.1 | blond | blue | moderate | moderate | 4-5 |
| | | | middle blond | blue | moderate | moderate | 4-5 |
| | | | Bleached | blue | good | good | 4 |
| B9 | A8 | 0.5 | blond | blue | good | good | 4-5 |
| | | | middle blond | blue | good | good | 4-5 |
| | | | Bleached | blue | good | good | 4 |

Mixtures of Polymeric Dyes:

A dye emulsion, pH=10.5

| INGREDIENT | w/w % |
|---|---|
| Mixture of dyes as described in Tables 2 and 3 | x |
| Cetearyl Alcohol | 12.00 |
| Ceteareth-20 | 4.50 |
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735-Day at the Beach | 0.50 |
| Deionized Water 70° C. | ad 100.00 | is mixed with 1.5 wt. % of a 9% hydrogen peroxide solution and the mixture is immediately applied to a tress of brown hair.

After 30 minutes the tress is rinsed, shampooed, rinsed and dried.

The color of the dyed tresses is given in Tables 2 and 3.

TABLE 2

Mixtures of polymeric dyes

| Comp. of formula | Color | B20 | B21 | B22 | B23 | B24 |
|---|---|---|---|---|---|---|
| A28-WO08009579[2] | yellow | 0.1 | 5.0 | | | 0.03 |
| A23-WO08009579[2] | orange | 1.0 | | 0.4 | 0.07 | |
| A7-WO08009579[2] | red | | 0.5 | | | 0.03 |
| A3 | red | | | 0.3 | | |
| A15-WO08009579[2] | red | | | | 0.01 | |
| A6 | blue | 1.0 | | | | 0.03 |
| A7 | blue | | 2.0 | | | |
| A8 | blue | | | 0.1 | | |
| A40 | blue | | | | 0.03 | |
| Total dye content X | | 0.3 | 7.5 | 0.8 | 0.11 | 0.09 |
| Color result on bleached hair[1] | | S | B | B | B | B |

[1] S = black, B = brown
[2] Polymeric dyes described in patent application no. WO08009579

TABLE 3

Mixtures of polymeric dyes and direct dyes.

| Comp. of formula | Color | B25 | B26 | B27 | B28 | B29 | B30 | B31 | B32 |
|---|---|---|---|---|---|---|---|---|---|
| A3 | red | 0.2 | | | | | | | |
| A7 | blue | | 2.0 | | 0.2 | | 1.6 | 0.1 | 0.2 |
| A8 | blue | 0.1 | | 0.5 | | 1.0 | | | |
| Direct Dye | | | | | | | | | |
| Basic Yellow 57 | | | 5.0 | | | 0.4 | 2.0 | 0.5 | |
| Basic Red 76 | | | | | 0.2 | | 0.3 | | |
| HC Red No. 3 | | | | 0.1 | | | 0.1 | | |
| HC Red BN | | | 0.5 | | | | 0.1 | | 0.1 |
| Basic Brown 16 | | 0.1 | | | | 0.5 | | | |
| Basic Brown 17 | | 0.1 | | | | 0.5 | | 2.0 | 0.5 |
| Basib Blue 99 | | | | | 0.01 | | | | |
| Total dye content X | | 0.5 | 7.5 | 0.6 | 0.4 | 2.41 | 0.5 | 0.3 | 0.8 |
| Color result on bleached hair[1] | | B | B | V | V | B | S | G | B |

[1] S = black, B = brown, V = violet, G = green

The invention claimed is:

1. Polymeric dye comprising oligo and polypeptides selected from natural or synthetic aminoacids bearing at least one covalently bounded cationic dye.

2. Polymeric dye according to claim 1 of formula

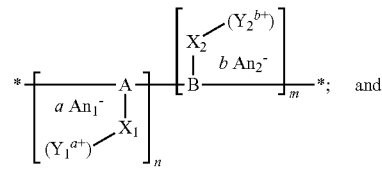

(1a)

-continued

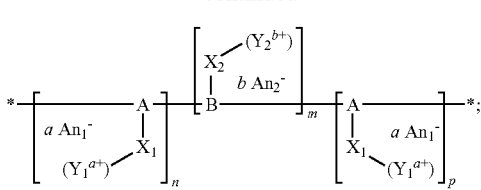
(1b)

wherein

A and B, independently from each other represent a polymer backbone selected from a natural or synthetic amino carboxylic acid;

$X_1$ and $X_2$ independently from each other are a linkage group selected from —$C_1$-$C_{30}$alkylene-, —$C_2$-$C_{12}$alkenylene-, or —$C_6$-$C_{10}$arylene- which is interrupted and/or terminated at one or both ends by one or more than one —O—, —S—, —N—, —N=—, —N($R_5$)—, —S(O)—, —$SO_2$—, —($CH_2CH_2$—O)$_{1-5}$—, —($CH_2CH_2CH_2$—O)$_{1-5}$—, —C(O)—, —C(O)O—, —OCO—,

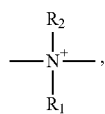

—CON($R_1$)—, —C($NR_1R_2$)$_2$—, —($R_1$)NC(O)—, —C(S)$R_1$— or

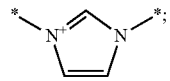

or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$ arylene), hydroxy or halogen; the direct bond; or a bivalent radical of formula -(T)$_t$(Z)—, wherein (1c)

T is —$C_1$-$C_{12}$alkylene; —$C_2$-$C_{12}$alkenylene-; —C(O)—; —($CH_2CH_2$—O)$_{1-5}$—; —($CH_2CH_2CH_2$—O)$_{1-5}$—; —C(O)O—; —OC(O)—; —N($R_3$)—; —CON($R_3$)—; —($R_3$)NC(O)—; —O—; —S—; —S(O)—; —S(O)$_2$—; —S(O)$_2$N($R_3$)—; or —N$^+$($R_3$)($R_4$)—;

Z is a biradical of formula

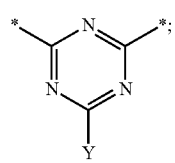
(1d)

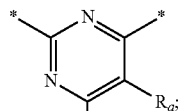
(1e)

or

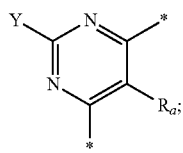
(1f)

$R_1$, $R_2$, $R_3$, $R_4$ and $R_5$ independently from each other are hydrogen; unsubstituted or substituted, straight-chain or branched, monocyclic or polycyclic, interrupted or uninterrupted $C_1$-$C_{14}$alkyl; $C_1$-$C_{14}$alkoxy; $C_2$-$C_{14}$alkenyl; $C_1$-$C_6$alkylamino; $C_6$-$C_{10}$aryl; $C_6$-$C_{10}$aryl-$C_1$-$C_{10}$alkyl; $C_6$-$C_{10}$aryl-$C_1$-$C_{10}$alkoxy; or $C_5$-$C_{10}$alkyl($C_5$-$C_{10}$aryl);

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; $SO_2R_3$; chlorine; or fluorine;

Y is $R_a$; $Y_1^{a+}$; or $Y_2^{b+}$;

a and b independently from each other are 1, 2 or 3;

t is 0 or 1;

$Y_1$ and $Y_2$ independently from each other are a residue of an organic dye; or hydrogen; wherein at least one of $Y_1$ and $Y_2$ is a residue of an organic dye;

$An_1$ and $An_2$, independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

3. Polymeric dye according to claim 2, wherein in formulae (1a) and (1b) A and B, independently from each other represent a polymer backbone selected from a natural or synthetic amino carboxylic acid;

$X_1$ and $X_2$ independently from each other are a linkage group selected from —$C_1$-$C_{30}$alkylene- and —$C_2$-$C_{12}$alkenylene-, which is interrupted and/or terminated at one or both ends by one or more than one —S—, —N—, —N=—, —N($R_5$)—, —S(O)—, —$SO_2$—, —($CH_2CH_2$—O)$_{1-5}$—, —($CH_2CH_2CH_2$—O)$_{1-5}$—, —C(O)—, —C(O)O—, —OCO—,

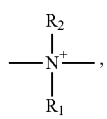

—CON($R_1$)—, —C($NR_1R_2$)$_2$—, —($R_1$)NC(O)—, —C(S)$R_1$—; or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen; the direct bond; or a bivalent radical of formula (1c) -(T)$_t$(Z)—, wherein T is —$C_1$-$C_{12}$alkylene; —$C_2$-$C_{12}$alkenylene-; —C(O)—; —($CH_2CH_2$—O)$_{1-5}$—; —($CH_2CH_2CH_2$—O)$_{1-5}$—; —C(O)O—; —OC(O)—; —N($R_3$)—; —CON($R_3$)—; —($R_3$)NC(O)—; —O—; —S—; —S(O)—; —S(O)$_2$—; —S(O)$_2$N($R_3$)—; or —$N^+$($R_3$)($R_4$)—;

Z is a biradical of formula

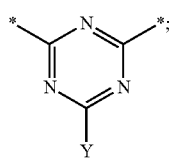

(1d)

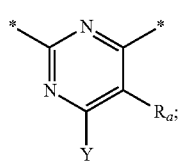

(1e)

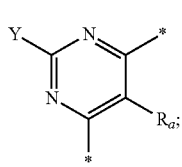

(1f)

$R_1$, $R_2$, $R_3$, $R_4$ and $R_5$ independently from each other are hydrogen; unsubstituted or substituted, straight-chain or branched, monocyclic or polycyclic, interrupted or uninterrupted $C_1$-$C_{14}$alkyl; $C_1$-$C_{14}$alkoxy; $C_2$-$C_{14}$alkenyl; $C_1$-$C_6$alkylamino; $C_6$-$C_{10}$aryl; $C_6$-$C_{10}$aryl-$C_1$-$C_{10}$alkyl; $C_6$-$C_{10}$aryl-$C_1$-$C_{10}$alkoxy; or $C_5$-$C_{10}$alkyl($C_5$-$C_{10}$aryl);

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; $SO_2R_3$; chlorine; or fluorine;

Y is $R_a$; $Y_1^{a+}$; or $Y_2^{b+}$;

a and b independently from each other are 1, 2 or 3;

t is 0 or 1;

$Y_1$ and $Y_2$ independently from each other are a residue of an organic dye; or hydrogen; wherein at least one of $Y_1$ and $Y_2$ is a residue of an organic dye;

$An_1$ and $An_2$, independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

4. Dye according to claim 1, wherein $Y_1$ and $Y_2$ independently from each other are selected from the group of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine, oxazine, perinone, perylene, pyrenequinone, phtalocyanine, phenazine, quinoneimine, quinacridone, quinophtalone, styryl, stilbene, xanthene, thiazine and thioxanthene dyes.

5. Dye according to claim 1, wherein $Y_1$ and $Y_2$ independently from each other are selected from azo, azomethine, hydrazomethine, anthraquinone, merocyanine, methine, oxazine and styryl dyes.

6. Dye according to claim 1, wherein $Y_1$ and $Y_2$ have the same meaning.

7. Dye according to claim 1, wherein both the polymer backbone (A and B) and residue of an organic dye ($Y_1$ and $Y_2$) have a functional group selected from the electrophilic group selected from halide, tosylate, mesylate, methoxy, carboxylic acid, carboxylic acid chloride, sulfonyl chloride, epoxides, anhydride; or a nucleophilic group selected from amine, guanidine, hydroxyl and thiol.

8. Dye according to claim 1, wherein the polymer backbone (A and B) is selected from histidine, arginine, cysteine, glutamine, glutaminic acid, lysine, asparagine, serine, tyrosine, threonine, tryptophane and proline.

9. Dye according to claim 1, wherein the polymer backbone is selected from polylysine, polyaspartic acid, polyglutamic acid and polyasparagin.

10. Dye according to claim 1, wherein the molecular weight of the polymeric dye is from 400 to 50000.

11. Dye according to claim 1, which correspond to a polylysine modified with a $X_1$_($Y_1^{a+}$) dye moiety in an α and/or ab ε position.

12. A composition comprising at least one dye of formula (1a) or (1b) as defined in claim 1.

13. A composition according to claim 12 comprising in addition at least one single further direct dye and/or an oxidative agent.

14. A composition according to claim 12 in the form of a shampoo, a conditioner, a gel or an emulsion.

15. A method of dyeing organic material, which comprises treating the organic material with at least one dye of formula (1a) or (1b) according to claim 1.

16. A method according to claim 15, which comprises treating the organic material with at least one dye of formula (1a) or (1b) as defined in claim 1 and an oxidative agent and optionally a further direct dye.

17. A method according to claim 15, which comprises treating the organic material with at least one compound of formula (1a) or (1b) and at least one single oxidative dye, or treating the organic material with a dye of formula (1a) or (1b) and at least one single oxidative dye and an oxidative agent.

18. A method according to claim 15 wherein the organic material is selected from keratin-containing fibers.

19. A method according to claim 18 wherein the keratin-containing fiber is human hair.

20. A method of dyeing organic material, which comprises treating the organic material with at least one dye of formula (1a) or (1b) according to a composition according to claim 12.

* * * * *